(12) United States Patent
Greer

(10) Patent No.: US 8,574,501 B1
(45) Date of Patent: Nov. 5, 2013

(54) NATURAL GAS TO LIQUID FUELS

(71) Applicant: Greenway Innovative Energy, Inc., Fort Worth, TX (US)

(72) Inventor: F. Conrad Greer, Fort Worth, TX (US)

(73) Assignee: Greenway Innovative Energy, Inc., Fort Worth, TX (US)

(*) Notice: Subject to any disclaimer, the term of this patent is extended or adjusted under 35 U.S.C. 154(b) by 0 days.

(21) Appl. No.: 13/769,079

(22) Filed: Feb. 15, 2013

Related U.S. Application Data

(63) Continuation-in-part of application No. 13/472,793, filed on May 16, 2012.

(51) Int. Cl.
*B01J 19/00* (2006.01)
*B01J 8/00* (2006.01)
*B01J 8/02* (2006.01)
*B01J 35/02* (2006.01)
*C07B 63/02* (2006.01)
*C07C 27/26* (2006.01)

(52) U.S. Cl.
USPC ........... 422/129; 422/187; 422/198; 422/211; 422/600; 48/61; 518/726

(58) Field of Classification Search
USPC ........ 48/61; 422/129, 187, 198, 211, 19, 600; 518/726
See application file for complete search history.

(56) References Cited

U.S. PATENT DOCUMENTS

| | | | |
|---|---|---|---|
| 4,199,533 A | | 4/1980 | Benson |
| 4,547,607 A | | 10/1985 | Jones et al. |
| 4,704,496 A | | 11/1987 | Paparizos et al. |
| 4,801,762 A | | 1/1989 | Leyshon |
| 5,093,542 A | | 3/1992 | Gaffney |
| 5,157,189 A | | 10/1992 | Karra |
| 5,245,124 A | | 9/1993 | Miremadi et al. |
| 7,500,999 B2 * | | 3/2009 | Aaron et al. .......... 48/127.9 |
| 2003/0225169 A1 | | 12/2003 | Yetman |
| 2004/0173501 A1* | | 9/2004 | Lawson et al. .......... 208/15 |
| 2009/0221723 A1* | | 9/2009 | Leviness .......... 518/709 |
| 2013/0068431 A1* | | 3/2013 | Ho et al. .......... 165/163 |

* cited by examiner

*Primary Examiner* — Walter D Griffin
*Assistant Examiner* — Natasha Young
(74) *Attorney, Agent, or Firm* — Fogarty, L.L.C.

(57) ABSTRACT

A method and apparatus for converting natural gas from a source, such as a wellhead, pipeline, or a storage facility, into hydrocarbon liquid stable at room temperature, comprising a skid or trailer mounted portable gas to liquids reactor. The reactor includes a preprocessor which desulfurizes and dehydrates the natural gas, a first stage reactor which transforms the preprocessed natural gas into synthesis gas, and a liquid production unit using a Fischer-Tropsch or similar polymerization process. The hydrocarbon liquid may be stored in a portable tank for later transportation or further processed on site.

21 Claims, 5 Drawing Sheets

NATURAL GAS TO LIQUID FUELS

RELATED APPLICATIONS

This application is a continuation-in-part of pending U.S. patent application Ser. No. 13/472,793, filed May 16, 2012, and titled Gas to Liquid Fuels, the disclosure of which is hereby incorporated by reference herein in its entirety.

BACKGROUND

The oil and gas industry is faced with the need to produce more fossil energy or to prove that the production of such energy is possible. Efforts expended heretofore in this regard have, among other things, revealed that a considerable amount of fossil energy may be obtained from shale deposits, which were previously thought to be only barriers to the migration of subterranean hydrocarbons. Rather recently it has been learned that many of the same shales, whose only function was thought to serve as a caprock or impermeable barrier to subterranean hydrocarbon migration, in fact, have served as massive agents to absorb natural gas. This natural gas can be converted to commercial production. Following drilling and fracturing the shale, so much of this type of unconventional gas production has been proven up at this point in time that the supply has exceeded the demand and prices of natural gas have diminished significantly.

Many operators who have paid the cost to drill, such as operators in the Barnett Shale in the area of Fort Worth, North Tex., have shut in their successful shale gas wells because the market price of the gas has fallen below acceptable economic levels for the operation of such wells. Therefore, there is a need to enhance the natural gas market and thereby encourage added drilling aimed at improving the natural gas reserves.

Gas to Liquid (GTL) technology for converting natural gas, which consists primarily of methane, to a liquid fuel has existed for nearly a century. A recent resurgence of interest is providing significant advancements in the rapidly growing art. Prior art teaches that natural gas may be converted to higher molecular weight hydrocarbons by generally two techniques, either a direct transformation with an intermittent step of creating a synthesis gas (syngas) or a gas composed generally of hydrogen and carbon monoxide.

Direct transformation into higher molecular weight hydrocarbons may occur through pyrolysis, during which methane generally at 250° C. to 100° C. is passed through a catalyst in the absence of substantial amounts of oxygen. Processes and catalysts are described in U.S. Pat. Nos. 4,199,533; 4,547,607; 4,704,496; 4,801,762; 5,093,542; 5,157,189; and 5,245,124. These processes require high activation energy and can be difficult to control. As a result, there is minimal commercial use of direct GTL processes.

Two or three GTL processes where the natural gas is first converted to syngas have more prevalent commercial use than the direct processes. For example, Mobil has developed M-gasoline which is created by a three stage process. Natural gas is converted to syngas which is transformed into methanol which is finally made into M-gasoline. However, the most common GTL process is a two stage process in which the natural gas is first converted to syngas which is then changed into liquid hydrocarbons via the Fischer-Tropsch process.

SUMMARY

The embodiments described herein are based upon a process that first removes sulfur compounds from natural gas, and then converts the processed gas using a catalyst-aided process to a liquid that is useable for transportation or other fuel. This process may be performed in a relatively small unit that could be portable, skid mounted, and/or located adjacent to a source of the natural gas. The liquid to which the natural gas is expected to be converted is anticipated to be a sulfur free mixture of various fuels: for example, gasoline, diesel fuel, jet fuel, and light bunker fuel. This mixture of fuels may then be separated to render them commercially saleable. Therefore, a third process involves the use of a small skid-mounted fractionation tower to separate and stabilize the various fuel products.

The skid-mounted conversion unit and processing equipment may be readily moved to any location where fuel is needed and where the gas can be piped to the skid. In an alternative embodiment, the skid may be placed at natural gas supply location, such as at a gas wellhead, pipeline, storage facility, or the like.

BRIEF DESCRIPTION OF THE DRAWINGS

Figure 1:
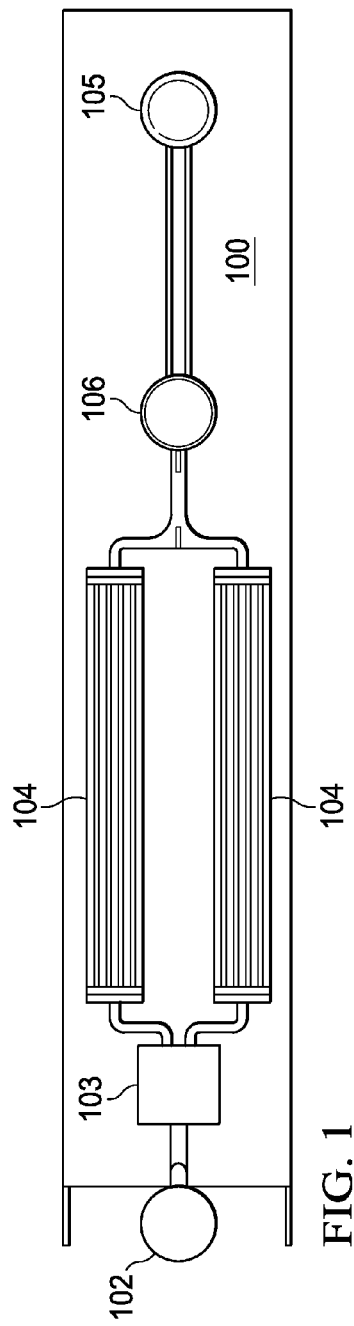

Having thus described the invention in general terms, reference will now be made to the accompanying drawings, which are not necessarily drawn to scale, and wherein:

FIG. 1 is a top view of one embodiment of an apparatus comprising a heavy duty truck trailer with a gas to liquids (GTL) conversion unit for transforming natural gas into a liquid phase at ambient temperature and pressure.

Figure 2:
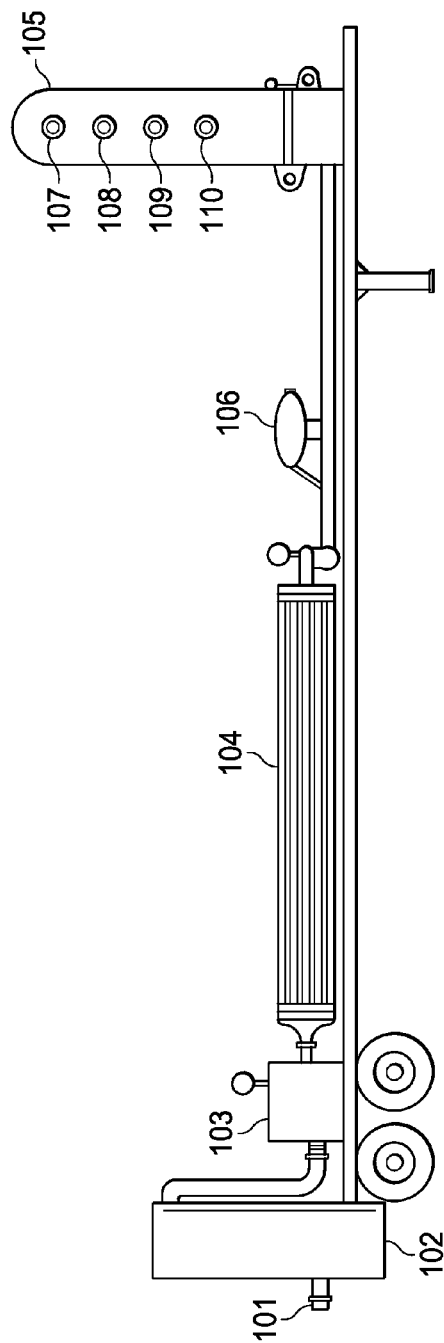

FIG. 2 is a side view of one embodiment of the apparatus of FIG. 1.

Figure 3:
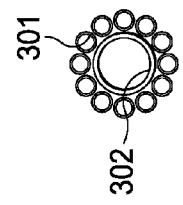

FIG. 3 is a cross-section of one embodiment of a Fischer-Tropsch reactor.

Figure 4:
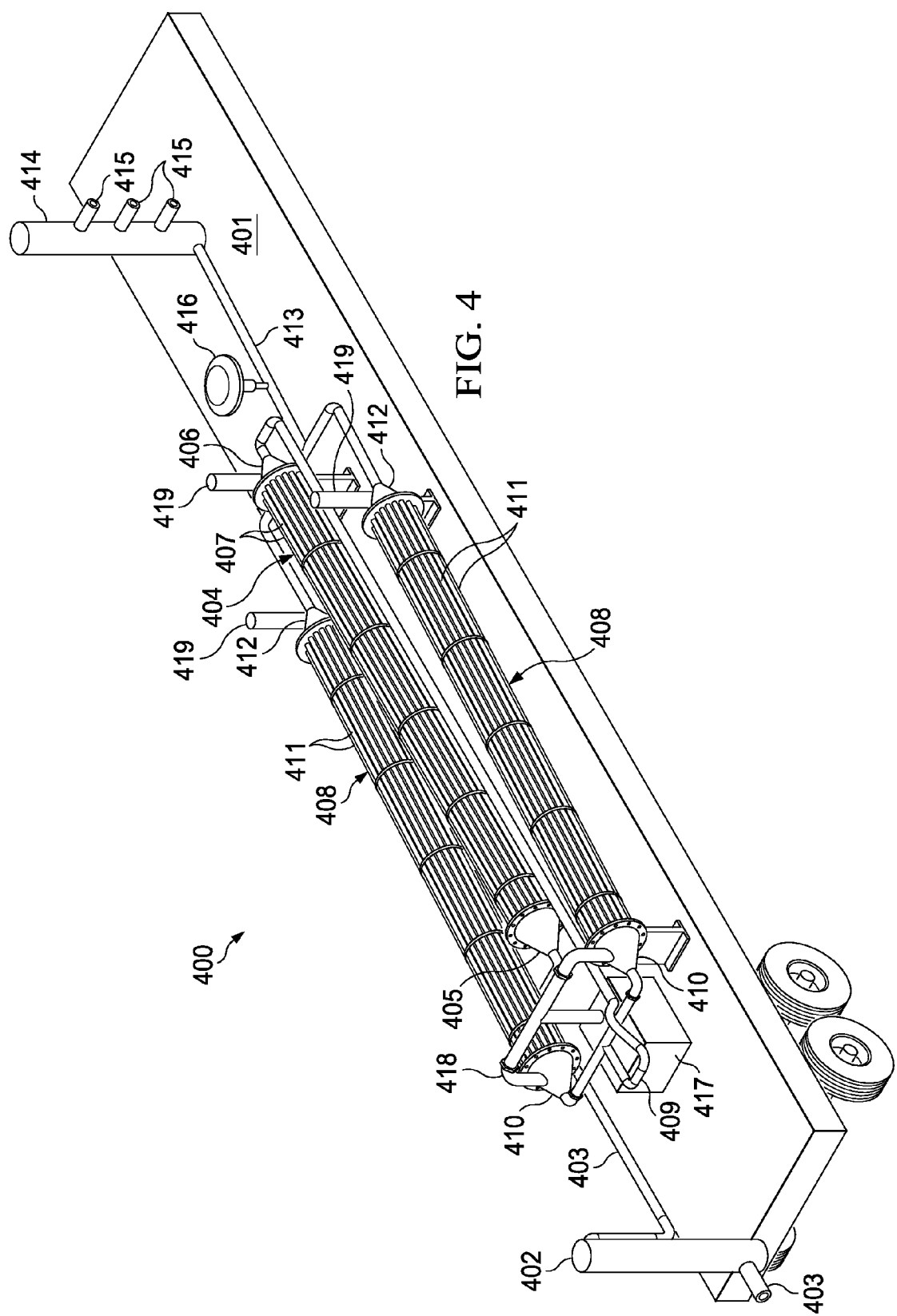

FIG. 4 illustrates an alternative embodiment of a portable GTL apparatus.

Figure 5:
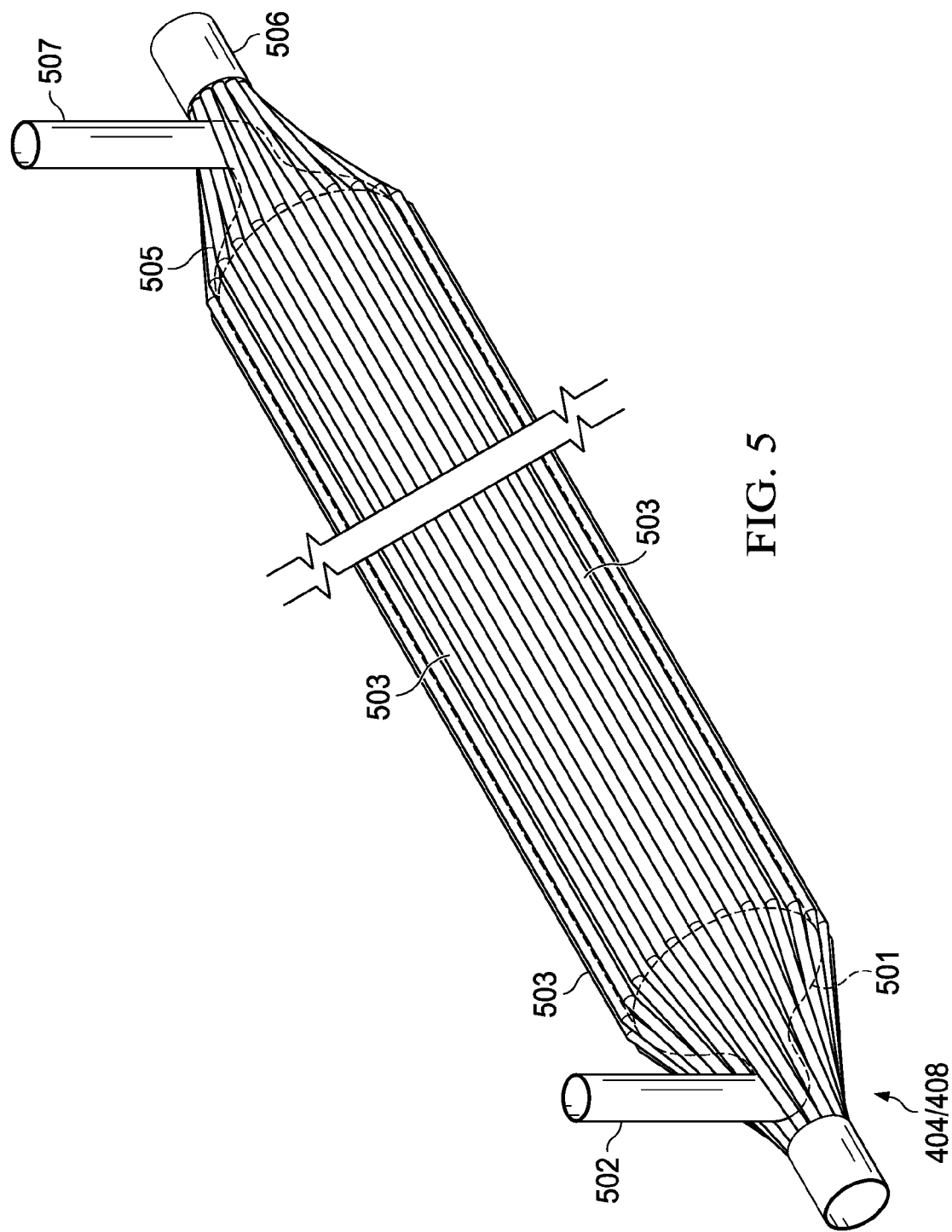
Figure 6:
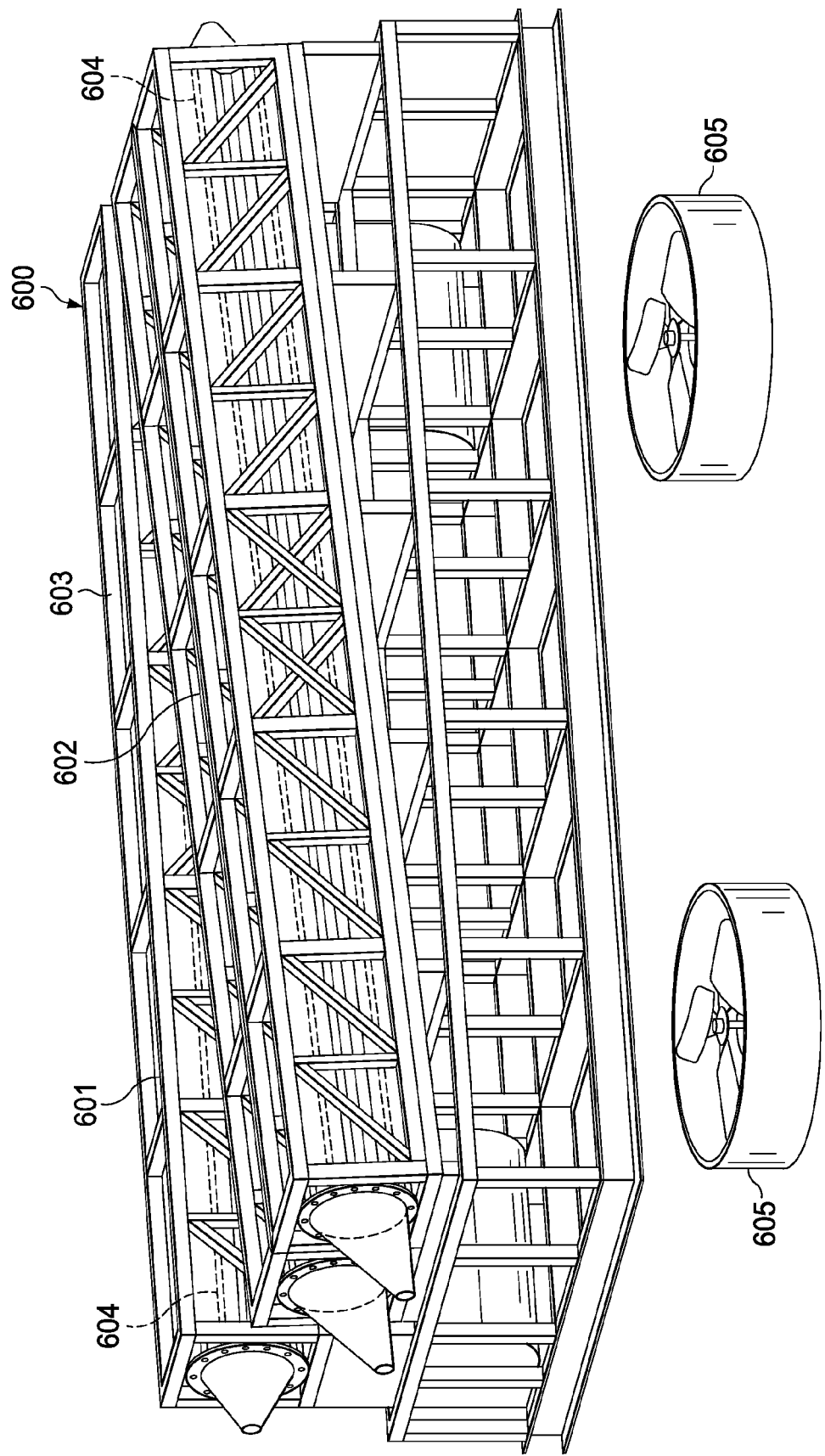
Figure 7:
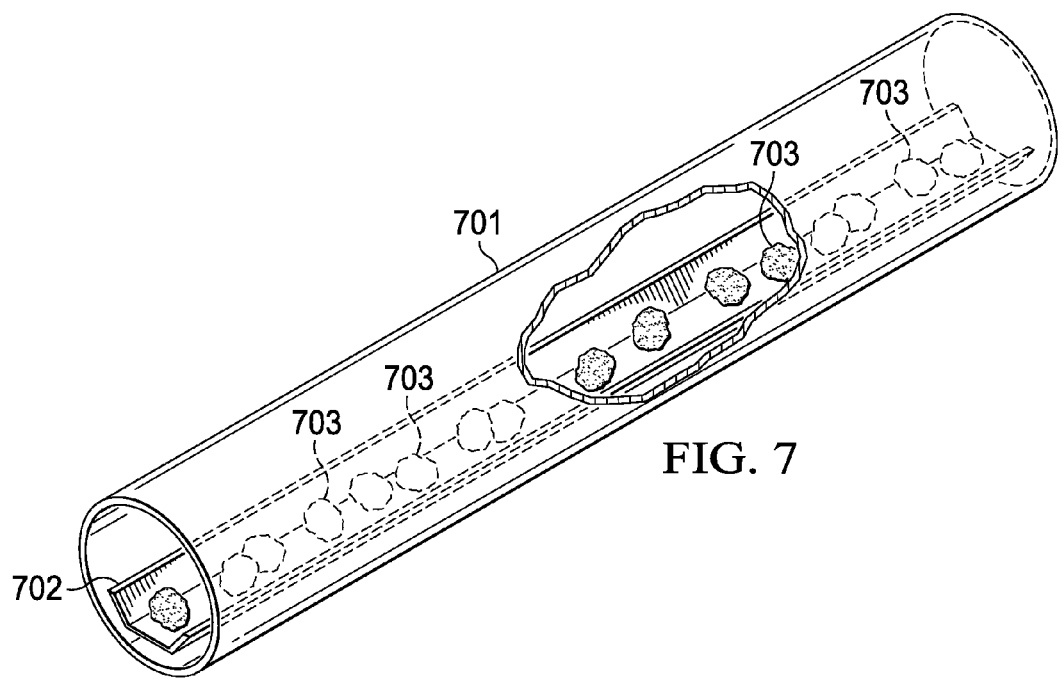

FIG. 5 illustrates a hydrogenation unit and Fischer-Tropsch reactors according to one embodiment FIG. 6 illustrates an alternative embodiment of a hydrogenation unit and Fischer-Tropsch reactors FIG. 7 illustrates an apparatus for holding catalyst within a hydrogenation unit and/or Fischer-Tropsch reactor pipe or tube.

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

The embodiments disclosed herein relate generally to a method and apparatus for converting sulfur-free natural gas to a non-cryogenic liquid for storage and/or transport by land vehicle to another location or for conversion to a motor fuel on-site. A large number of stranded gas fields exist, meaning that they are not close enough to a pipeline to be economically feasible for production. As a consequence, such fields may not be economically developed and the economic value of the gas remains trapped in the earth's crust. Oil wells on the other hand can be developed even if such wells are in a remote location because the liquid oil may be accumulated in a designated tank placed at the well location and then transferred to a refinery by a tanker truck. In some cases, natural gas may be available at a remote location, for example, in a pipeline. However, such natural gas has greater utility if converted in situ to a liquid motor fuel.

The apparatus may comprise at least one truck trailer, a desulfurizing unit, a gas to liquid conversion unit for transforming natural gas into hydrocarbon, characterized by having a liquid phase at atmospheric pressure and ambient temperature, said gas to liquid conversion unit on top of said truck trailer and fastened thereto. A natural-gas-driven electric generator sufficient to provide electricity for all requirements of the truck trailer and the equipment mounted on the truck trailer may also be provided on the truck trailer.

FIG. 1 is a top-view illustration of an apparatus comprising at least one heavy-duty truck trailer 100 with a gas to liquids (GTL) conversion unit for transforming natural gas into a liquid phase at ambient temperature and pressure according to one embodiment. FIG. 2 is a side view of the apparatus. The GTL conversion unit is designed and outfitted for filtering, desulfurizing, dehydrating, and regulating the pressure of the gas and liquid processed by the apparatus. The gas to liquid conversion unit comprises a first stage reactor 103 for converting the effluent of pipeline quality gas into synthesis gas by a hydrogenation source, such as a steam methane reformer, hydrogen generator, hydrogen tank, or auto thermal reformer, and a Fischer-Tropsch reactor 104 for polymerizing said synthesis gas to produce said liquid hydrocarbon.

The gas to liquid conversion unit of the apparatus is characterized by having catalyst sites that are designed and arranged with high surface-area to volume ratios.

The gas to liquid conversion unit comprises a gas preprocessing section for filtering, desulfurizing, dehydrating, and regulating the pressure of said unit. A first stage converts the effluent of said gas preprocessing unit into synthesis gas by a hydrogen generation process or source, such as a steam methane reforming reaction. Thereafter, the gas is conducted through a Fischer-Tropsch reactor to polymerize said synthesis gas to produce liquid.

The apparatus further comprises one or more storage tanks into which the liquid fuels emanating from a fractionation tower may be temporarily stored until they are delivered to a collection tank truck.

In one embodiment, a method for converting natural gas at remote terrestrial sources to hydrocarbon is characterized by having a liquid phase at atmospheric pressure and ambient temperature, comprising the steps of moving the trailer mounted GTL equipment in close proximity to the gas source, coupling the equipment to the gas source, and conducting natural gas through the gas to liquid conversion unit while located near said source.

Referring to FIG. 1, the apparatus comprises a natural gas inlet 101 that may be coupled to a natural gas source, such as a natural gas well or a pipe line. Natural gas flows through the inlet 101 to a sulfur gas removal unit 102, which is loaded with iron shavings in one embodiment. The natural gas flows over the iron filings in desulfurization unit 102, which removes the sulfur content from the natural gas. The removal of sulfur from the natural gas improves the lifetime of the catalysts, such as that used in the Fischer-Tropsch reactions. For sulfur in the form $H_2S$, the iron shavings react with the sulfur in the natural gas to form $FeS_2$. Depending on the content of the sulfur in the natural gas source any other suitable desulfurization unit 102 that is adapted to remove sulfur from natural gas may be used.

The output of sulfur gas removal unit 102 is provided to a hydrogenation unit 103, such as a steam methane reformer that is loaded with a Nickel catalyst. In other embodiments, any hydrogen source generator may be used in place of a steam methane reformer, such as a hydrogen generator, an auto thermal reformer, or a tank of commercially available hydrogen gas.

The output of hydrogenation unit 103 is input to Fischer-Tropsch reactors 104. In the case where a steam methane reformer is used as hydrogenation unit 103, the Fischer-Tropsch reactors 104 will cause the methane molecule to act as follows: $CH_4+H_2O \rightarrow CO+3H_2$. The reactant products are converted from natural gas to a liquid as the substance passes through the Fischer-Tropsch reactors 104. The long chain hydrocarbon molecules structure produced by the Fischer-Tropsch reactors may vary depending on the hydrogen source selected.

A cross section of one embodiment of Fischer-Tropsch reactor 104 is shown in FIG. 3. Fischer-Tropsch reactors 104 comprise sections of 1" extra heavy (XH) line pipe 301 wrapped around a 16" lightweight center pipe 302. The 1" XH line pipe may be loaded with Ruthenium catalyst to effect a Fischer-Tropsch reaction. In other embodiments, a Cobalt catalyst or any other suitable catalyst that will effect a Fischer-Tropsch reaction may be used. Ambient air may be circulated through the 16" pipe 302 to control the system temperature. In other embodiments, the pipes 301 in the Fischer-Tropsch reactor 104 may be arranged in other configurations that allow air to circulate for cooling. The Fischer-Tropsch reactors 104 may be air cooled using any method of air generation including, for example, high velocity fans. Additionally, water may be used as a coolant and may enhance the reactant process.

The Fischer-Tropsch reactors 104 may be positioned at an angle (e.g., at a 3° slope) to cause the liquid to flow through the reactors toward a fractionation tower 105. The output of Fischer-Tropsch reactors 104 passes through a gas trap (not shown). Any gases trapped in the gas trap are recirculated to the front of the Fischer-Tropsch reactors 104 for further GTL processing. A back-pressure control valve 106 is positioned on the pipe linking the Fischer-Tropsch reactors 104 to the fractionation tower 105 in order to control the pressure, flow rate and temperature into fractionation tower 105. In one embodiment, fractionation tower 105 may be hinged or otherwise adapted to be rotated from a vertical position for transport of the apparatus in order to avoid low hanging structures or wires.

By the time the reactant products reach the base of the fractionation tower 105, the reactant products are hot liquids capable of boiling and, as such, the products will be segregated as they cool in the fractionation tower 105. Fractionation tower 105 may have a number of outlets, such as an outlet 107 to a gasoline storage tank, an outlet 108 to a diesel storage tank, an outlet 109 to an aviation fuel storage tank, and an outlet 110 to a heavier fuel storage tank.

FIG. 4 illustrates an alternative embodiment of a portable GTL apparatus 400. The GTL equipment is mounted on a truck trailer, skid, pallet, or other portable or mobile platform 401 that allows it to be moved and deployed near natural gas sources, such as gas wellhead, pipeline, storage tank, or other location or facility. The portable platform 401 may be driven, dragged, pushed, airlifted, floated, or otherwise moved to a natural gas source in any location whether easily accessible or remote. A desulfurization unit 402 has an inlet 403 that may be coupled to the natural gas source. Desulfurization unit 402 may use iron filings, for example, to react with and remove sulfur from the natural gas. The natural gas output from desulfurization unit 402 is fed by pipe 403 to a hydrogenation unit 404.

The desulfurized natural gas passes through a hydrogenation unit 404 from input 405 to output 406. In one embodiment, hydrogenation unit 404 comprises twenty-nine 1" pipes 407 surrounding a 16" central pipe (not shown). The twenty-nine 1" pipes contain a Nickel catalyst that reacts with the natural gas to generate hydrogen ($H_2$) molecules. The natural gas and hydrogen is provided to two Fischer-Tropsch reactors 408 by pipe 409. In other embodiments, hydrogenation unit 404 may be, for example, a steam methane reformer, an auto thermal reformer, or a hydrogen tank that generates or provides hydrogen to mix with the natural gas.

The natural gas and hydrogen enter the Fischer-Tropsch reactors 408 at inputs 410. In one embodiment, Fischer-Tropsch reactors 408 each comprise twenty-nine 1" pipes 411 surrounding a 16" central pipe (not shown). The twenty-nine 1" pipes contain a catalyst, such as Ruthenium or Cobalt, that effect a Fischer-Tropsch process so that the natural gas and hydrogen is converted to liquid at exits 412. The Fischer-Tropsch reactors 408 are constructed at an angle, such as a 3° angle, so that the liquid will flow from input 410 toward output 412.

The liquid is then provided by pipe 413 to a fractionation tower 414. The liquid rises in fractionation tower 414 and is output at a port 415 selected depending upon the desired liquid fuel type. A valve 416 on pipe 413 may be used to regulate the pressure output from Fischer-Tropsch reactors 408 and input to fractionation tower 414.

It is expected that the temperatures created in hydrogenation unit 404 and the Fischer-Tropsch reactors 408 will be very high. For example, a hydrogenation unit 404 using a Nickel catalyst as described above may operate at approximately 800° C. and the Fischer-Tropsch reactors 408 may operate at approximately 300° C. Therefore, hydrogenation unit 404 and the Fischer-Tropsch reactors 408 will likely require cooling. In one embodiment, hydrogenation unit 404 and the Fischer-Tropsch reactors 408 are air-cooled by an air source 417, such as a fan, blower, or turbine that provides air to the center 16" pipe of the hydrogenation unit 404 and the Fischer-Tropsch reactors 408 via air pipes 418. The air flows though the center pipe to cool the respective hydrogenation unit 404 and/or the Fischer-Tropsch reactor 408. The cooling air exits the hydrogenation unit 404 and the Fischer-Tropsch reactors 408 via exhaust 419.

FIG. 5 illustrates the hydrogenation unit 404 and Fischer-Tropsch reactors 408 according to one embodiment. A central 16" pipe receives air at input 502 from an air source. Twenty-nine 1" pipes 503 are wrapped around the center pipe 501. Catalyst, such as Nickel in a hydrogenation unit 404 or Ruthenium or Cobalt in a Fischer-Tropsch reactor 408, is placed in the twenty-nine pipes 503. Any other catalyst proven to affect the desired reaction(s) may be used in the alternative. An input manifold 504 distributes the incoming natural gas (hydrogenation unit 404) or natural gas and hydrogen (Fischer-Tropsch reactors 408) to the twenty-nine pipes 503. An output manifold 505 collects the output natural gas and hydrogen (hydrogenation unit 404) or liquid (Fischer-Tropsch reactors 408) and provides the output to pipes 409 or 413, respectively, at outlet 506. Cooling air exits the assembly via outlet 507.

FIG. 6 illustrates an alternative embodiment of the hydrogenation unit 601 and Fischer-Tropsch reactors 602. Instead of wrapping the 1" pipes around a center pipe for cooling as illustrated in FIGS. 1, 4, and 5, the 1" pipes 604 are held in bracket-like structure 600 that provides spacing between the 1" pipes 604 so that air can flow between the pipes 604 for cooling. An air source 605, such as fans, blowers, or turbines, is used to provide ventilation through the bracket structure 600 and across pipes 604 for cooling.

It will be understood that other cooling arrangements, such as water cooling, may be used for the hydrogenation unit and Fischer-Tropsch reactors depending upon the configuration of the system. Additionally, it will be understood that the embodiments illustrated herein are merely examples and that the number of pipes, other pipe sizes and other configurations may be used for the hydrogenation unit and Fischer-Tropsch reactors.

FIG. 7 illustrates an apparatus for holding catalyst within a hydrogenation unit and/or Fischer-Tropsch reactor pipe or tube. Each device, as illustrated above, comprises a plurality of pipes filled with a catalyst. Over time, the catalyst will become "poisoned" as other compounds bond to its active surface sites, which reduces the usefulness of the catalyst. When that occurs, the catalyst in the hydrogenation unit and/or Fischer-Tropsch reactor will need to be replaced. In order to simplify the replacement of the catalyst within the pipes 701 of these devices, a tray 702 is adapted to carry the catalyst 703. This makes it easier to load, unload, and replace the catalyst. The operator simply has to load the catalyst 703 on the tray 702 and inserts the tray 702 into a pipe 701 of the hydrogenation unit or Fischer-Tropsch reactor (e.g., pipes 301 (FIG. 3) or 503 (FIG. 5)).

The catalyst 703 may have any appropriate form that is required by the process or available from a manufacturer, such as pellets, disks, rings, or other shapes. Tray 702 may be adapted to hold a particular form of the catalyst in a desired position, for example, to maximize an available surface area exposure or to generate turbulence or to otherwise improve the desired reaction. Tray 702 may also be adapted to evenly distribute the catalyst in pipe 701 and to prevent unwanted shifting of the catalyst during movement of the GTL apparatus. In one embodiment, trays 702 extend the entire length of the pipe 701 and provide for easy loading and uniform flow of hydrogen over the catalyst 703 in order to maximize contact with the catalyst and provide uniformity of reaction.

In other embodiments a series of trays 702 may be used in a pipe 701 instead of a single long tray.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention. While preferred embodiments of the invention have been described, modifications and adaptations of the preferred embodiments will occur to those skilled in the art. It is to be expressly understood that modifications and adaptations are in the spirit and scope of inventions set forth in the following claims.

What is claimed is:

1. A mobile or portable apparatus, comprising:
   a hydrogenation unit having an input configured to receive natural gas;
   a Fischer-Tropsch reactor having an input coupled to an output of the hydrogenation unit, the Fischer-Tropsch reactor comprising a plurality of catalyst-filled pipes wrapped around a center cooling pipe; and a fractionation tower having an input coupled to an output of the Fischer-Tropsch reactor, the fractionation tower having one or more outputs for liquid hydrocarbons.

2. The apparatus of claim 1, further comprising:
a natural gas powered electric generator.

3. The apparatus of claim 1, further comprising:
a desulfurization unit having an input adapted to receive natural gas, the desulfurization unit configured to remove sulfur from the natural gas, the desulfurization unit having an output coupled to the input of the hydrogenation unit.

4. The apparatus of claim 1, wherein the hydrogenation unit is selected from the group consisting of:
a hydrogen generator;
a steam methane reformer;
an auto thermal reformer; and
a hydrogen tank.

5. The apparatus of claim 1, wherein the catalyst-filled pipes further comprise a Ruthenium or Cobalt catalyst.

6. The apparatus of claim 1, wherein the Fischer-Tropsch reactor further comprises:
an air source configured to blow air through the center cooling pipe.

7. The apparatus of claim 1, wherein the one or more fractionation tower outputs are located at different heights, each of the outlets adapted to output a liquid hydrocarbon corresponding to a different liquid fuel type.

8. The apparatus of claim 1, wherein the hydrogenation unit is configured to convert natural gas into a synthesis gas; and wherein the Fischer-Tropsch reactor is configured to polymerize the synthesis gas and to produce a liquid hydrocarbon.

9. The apparatus of claim 1, wherein the hydrogenation unit or the Fischer-Tropsch reactor or both are water-cooled.

10. The apparatus of claim 1, further comprising:
a storage tank for collecting said liquid hydrocarbons.

11. A mobile or portable apparatus, comprising:
a hydrogenation unit having an input configured to receive natural gas, the hydrogenation unit comprising a plurality of catalyst-filled pipes wrapped around a center cooling pipe;
a Fischer-Tropsch reactor having an input coupled to an output of the hydrogenation unit; and
a fractionation tower having an input coupled to an output of the Fischer-Tropsch reactor, the fractionation tower having one or more outputs for liquid hydrocarbons.

12. The apparatus of claim 11, wherein the catalyst-filled pipes further comprise a Nickel catalyst.

13. The apparatus of claim 11, wherein the hydrogenation unit further comprises:
an air source configured to blow air through the center cooling pipe.

14. The apparatus of claim 11, further comprising:
a storage tank for collecting said liquid hydrocarbons.

15. The apparatus of claim 11, further comprising:
a desulfurization unit having an input adapted to receive natural gas, the desulfurization unit configured to remove sulfur from the natural gas, the desulfurization unit having an output coupled to the input of the hydrogenation unit.

16. The apparatus of claim 11, wherein the one or more fractionation tower outputs are located at different heights, each of the outlets adapted to output a liquid hydrocarbon corresponding to a different liquid fuel type.

17. The apparatus of claim 11, wherein the hydrogenation unit is configured to convert natural gas into a synthesis gas; and wherein the Fischer-Tropsch reactor is configured to polymerize the synthesis gas and to produce a liquid hydrocarbon.

18. The apparatus of claim 11, wherein the hydrogenation unit is water-cooled.

19. The apparatus of claim 11, wherein the Fischer-Tropsch reactor is water-cooled.

20. The apparatus of claim 11, further comprising:
a natural gas powered electric generator.

21. A apparatus, comprising:
a desulfurization unit having an input adapted to receive natural gas, the desulfurization unit configured to remove sulfur from the natural gas;
a hydrogenation unit having an input configured to receive natural gas from the desulfurization unit, the hydrogenation unit comprising a plurality of catalyst-filled pipes wrapped around a center cooling pipe;
a Fischer-Tropsch reactor having an input coupled to an output of the hydrogenation unit, the Fischer-Tropsch reactor comprising a plurality of catalyst-filled pipes wrapped around a center cooling pipe;
an air source configured to blow air through the center cooling pipes of the hydrogenation unit and the Fischer-Tropsch reactor; and
a fractionation tower having an input coupled to an output of the Fischer-Tropsch reactor, the fractionation tower having one or more located at different heights, each of the outlets adapted to output a liquid hydrocarbon corresponding to a different liquid fuel type.

* * * * *